(12) United States Patent
Cheong et al.

(10) Patent No.: US 8,557,568 B2
(45) Date of Patent: Oct. 15, 2013

(54) METHOD AND APPARATUS FOR DISRUPTING CELLS AND AMPLIFYING NUCLEIC ACIDS USING GOLD NANORODS

(75) Inventors: Kwang Ho Cheong, Yongin-si (KR); Dong-kee Yi, Yongin-si (KR); Jeong-gun Lee, Yongin-si (KR); Jong-myeon Park, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 274 days.

(21) Appl. No.: 13/107,677

(22) Filed: May 13, 2011

(65) Prior Publication Data

US 2011/0212514 A1 Sep. 1, 2011

Related U.S. Application Data

(62) Division of application No. 11/838,550, filed on Aug. 14, 2007, now Pat. No. 7,972,819.

(30) Foreign Application Priority Data

Nov. 9, 2006 (KR) .......................... 10-2006-0110544

(51) Int. Cl.
*C12M 1/34* (2006.01)
*C12M 3/00* (2006.01)
*C12M 1/00* (2006.01)

(52) U.S. Cl.
USPC .................. 435/287.2; 435/285.3; 435/306.1; 435/283.1; 422/68.1

(58) Field of Classification Search
None
See application file for complete search history.

(56) References Cited

U.S. PATENT DOCUMENTS

| | | | |
|---|---|---|---|
| 6,685,730 B2 | 2/2004 | West et al. | |
| 7,892,491 B2 * | 2/2011 | Kim et al. | 422/68.1 |
| 2003/0096429 A1 | 5/2003 | Baeumner et al. | |
| 2009/0326614 A1 | 12/2009 | El-Sayed et al. | |

OTHER PUBLICATIONS

Day, et al. (1980) "Reversibility of Sodium-Induced Aggregation of Sonicated Phosphatidylserine vesicles", Proceedings of the National of Sciences, USA., 77(7): 4026-29.*
Lee, et al. (May 2, 2006) Microchip-Based One Step DNA Extraction and Real-Time PCR in one Chamber for Rapid Pathogen Identification, Lab Chip, 6: 886-95.*
Li, H. et al. (2001) Anal. Chem., 73: 4625-4631.*
Cheong, et al. (2008) "Gold nanoparticles for one step DNA extraction and real-time PCR of pathogens in a single chamber", Lab on a Chip, 8: 810-3.*
Li, H. et al., "Spatial Control of Cellular Measurements with the Laser Micropipet"; Anal. Chem., 2001, 73 (19): 4625-4631.
Taylor, M.T. et al., "Lysing Bacterial Spores by Sonication through a Flexible Interface in a Microfluidic System" (2001) Anal. Chem., 73(3): 492-496.
Mohamed, M. B., et al., "The "lightning" gold nanorods: fluorescence enhancement of over a million compared to the gold metal"; Chemical Physics Letters, 2000, vol. 317: 517-523.
Yu, Y., et al.; "Gold Nanorods: Electrochemical Synthesis and Optical Properties"; The Journal of Physical Chemistry B, 1997, vol. 101, No. 34: 6661-6664.
Jana, N. R., et al., "Wet Chemical Synthesis of High Aspect Ratio Cylindrical Gold Nanorods"; 2001, J. Phys. Chem. B; vol. 105: 4065-4067.
Kim, F., et al., "Photochemical Synthesis of Gold Nanorods"; J. Am. Chem. Soc., 2002; vol. 124: 14316-14317; Published on Web Nov. 9, 2002.
Huang, X. et al., Gold Nanorods: From Synthesis and Properties to Biological and Biomedical Applications, Adv. Mater. 2009, 21: 4880-4910.
Cheong, K.H. et al., Gold nanoparticles for one step DNA extraction and real-time PCR of pathogens in a single chamber, Lab Chip. May 2008;8(5): 810-813. Epub Mar. 11, 2008.

* cited by examiner

*Primary Examiner* — Robert M Kelly
(74) *Attorney, Agent, or Firm* — Cantor Colburn LLP

(57) ABSTRACT

Provided is a method of disrupting cells comprising adding gold nanorods to a solution containing cells and irradiating the gold nanorods with a laser to disrupt the cells. A method and an apparatus for continuously disrupting cells and amplifying nucleic acids in a single microchamber are also provided, wherein the method comprises introducing a solution containing cells and gold nanorods into a microchamber, irradiating a laser onto the gold nanorods to disrupt the cells, and amplifying a nucleic acid from the disrupted cells in the microchamber. The apparatus comprises a cell disruption chamber comprising a sample inlet, and gold nanorods introduced therein; a laser attached to the cell disruption chamber, wherein the laser is for generating light at a wavelength absorbed by the gold nanorods; and a heater and a cooler for heating and cooling the cell disruption chamber. Also disclosed is a lab-on-a chip comprising the apparatus.

9 Claims, 9 Drawing Sheets

METHOD AND APPARATUS FOR DISRUPTING CELLS AND AMPLIFYING NUCLEIC ACIDS USING GOLD NANORODS

CROSS-REFERENCE TO RELATED PATENT APPLICATIONS

This application is a division of U.S. application Ser. No. 11/838,550, filed Aug. 14, 2007, issued Jul. 5, 2011 as U.S. Pat. No. 7,972,819, which claims priority to Korean Patent Application No. 10-2006-0110544, filed on Nov. 9, 2006, the disclosure of which is incorporated herein in its entirety by reference.

BACKGROUND OF THE INVENTION

1. Field of the Invention

The present invention relates to a method and apparatus for disrupting cells or viruses using gold nanorods and amplifying nucleic acids released from the disrupted cells or viruses.

2. Description of the Related Art

Figure 1:
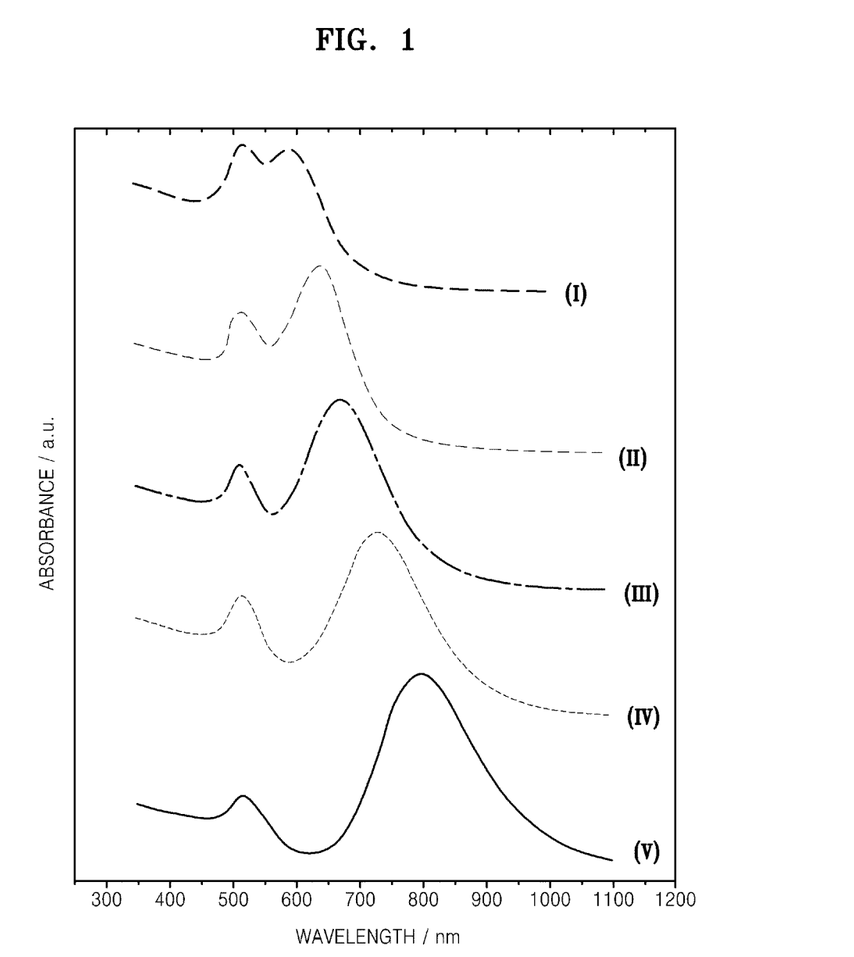
FIG. 1 is a graph of absorbance versus wavelength for conventional gold nanorods having length to diameter ratios of 2.0 (I), 2.6 (II), 3.3 (III), 4.3 (IV), and 5.4 (V), respectively.

Gold nanorods are gold nanoparticles in a rod form possessing good light absorption properties in the range of visible light to near infrared light. As illustrated in FIG. 1, it is known that the wavelength of light absorbed by gold nanorods varies according to a ratio of the cross-sectional diameter (hereinafter referred to as "diameter") to the length of the gold nanorods (Mohamed, M. B. et al. (2000) *Chemical Physics Letters*, 317: 517-523). For example, FIG. 1 illustrates the absorption spectra of gold nanorods having length to diameter ratios of 2.0, 2.6, 3.3, 4.3, and 5.4, (FIG. 1, (I), (II), (III), (IV), and (V) respectively).

Cell lysis is conventionally performed using a variety of methods including mechanical, chemical, thermal, electrical, ultrasonic or microwave methods (Taylor, M. T. et al. (2001) *Anal. Chem.*, 73: 492-496). Additionally, a laser provides many advantages for use in the disruption of cells and can be readily applied to Lab-on-a-Chip (LOC) methods (Li, H. et al. (2001) *Anal. Chem.*, 73: 4625-4631).

U.S. Patent Publication No. 2003/96429 A1 discloses a laser-induced cell lysis system. When only a laser is used, efficient cell lysis does not occur. For example, an experiment using *E. coli* placed in a very clear solution confirmed that when irradiating with only a laser, a low cell lysis efficiency was obtained. Further, the concentration of DNA measured after irradiating the cell sample with a laser for 150 seconds was 3.77 ng/µl, whereas the concentration of DNA measured after boiling cells in a comparable cell sample at 95° C. for 5 minutes was 6.15 ng/µl. The lower level of DNA obtained as the result of cell lysis by laser irradiation resulted because the laser energy was not effectively transferred to the cells.

U.S. Pat. No. 6,685,730 discloses optically-absorbing nanoparticles for enhanced tissue repair. This patent relates to a method of joining tissue comprising: delivering nanoparticles having dimensions of 1 to 1000 nanometers that absorb light at one or more wavelengths to the tissue to be joined; and exposing the nanoparticles to light at one or more wavelengths that are absorbed by the nanoparticles. This method of using a laser and nanoparticles causes only a loss of function in the cells. There is no description of a method for disrupting cells using a solution containing cells and gold nanorods.

A conventional Laser-Irradiated Magnetic Beads System (LIMBS) disrupts cells using micro-magnetic beads to obtain genetic materials. However, in this case, it is preferred that the magnetic beads be removed from the cellular material prior to subsequent downstream processes. To implement LIMBS in a Lab-on-a-Chip (LOC) method, a membrane for removing the beads should be used or alternatively, a surface structure should be manufactured other than beads, which results in additional costs and low efficiency. In addition, the magnetic beads can adsorb fluorescent materials that are used for real time polymerase chain reaction (PCR), such as SYBR Green dye, and thus, the use of these dyes has been limited.

Thus, the inventors conducted extensive research in order to address the above problems and discovered that micro-magnetic beads can be replaced with gold nanorods to remarkably increase the surface area, thereby improving the efficiency of disrupting cells or viruses, and attaining high levels of cell disruption, even when only small amounts of nanorods are used. In particular, gold nanorods were found to not significantly affect the optical properties of a solution. Although these nanomaterials are not removed after using them, genetic materials can be detected using subsequent real time PCR methods. PCR can be continuously performed without removing the gold nanorods following the disruption of cells or viruses.

SUMMARY OF THE INVENTION

The present invention provides a method of disrupting cells efficiently. The method comprises adding gold nanorods to a solution containing cells, and irradiating a laser onto the gold nanorods to disrupt the cells. The present invention also provides a method of continuously disrupting cells and amplifying nucleic acids in a single microchamber, comprising introducing a solution containing cells and gold nanorods into a microchamber; irradiating a laser onto the gold nanorods to disrupt the cells; and amplifying a nucleic acid from the disrupted cells in the microchamber.

The present invention also provides an apparatus for disrupting cells and amplifying nucleic acids in a signal microchamber comprising: a cell disruption chamber comprising a sample inlet, a laser attached to the cell disruption chamber, and a heater and a cooler for heating and cooling the cell disruption chamber.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

According to one embodiment, there is provided a method of disrupting cells, the method comprising: adding gold nanorods to a solution containing cells, and irradiating a laser onto the gold nanorods to disrupt the cells.

As used herein, the term "cell" means a microorganism, a prokaryotic or eukaryotic cell (e.g. a plant cell, a bacterial cell, a pathogenic cell, or a yeast cell), an aggregate of cells, a virus, a bacteriophage, a fungus, or other nucleic acid containing biological material, such as, for example, an organelle.

As used herein, the term "nucleic acid" means DNA, RNA, or a combination of both. The DNA or RNA can be in any possible configuration, i.e. in the form of double-stranded (ds) nucleic acid, or in the form of single-stranded (ss) nucleic acid, or as a combination thereof.

Figure 2:
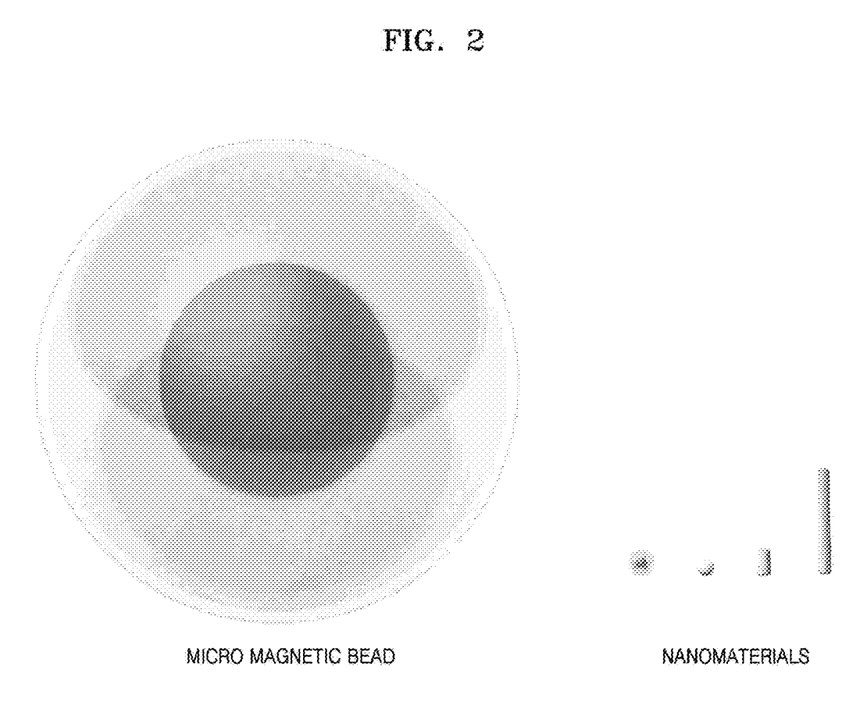
FIG. 2 is a schematic illustration comparing the sizes of exemplary nanomaterials and those of micro-magnetic beads.

The present invention relates to a method of disrupting cells using gold nanorods rather than conventional micro-magnetic beads. When a laser is irradiated onto gold nanorods in an aqueous solution, the temperature of the aqueous solution is more effectively increased than when using micro-magnetic beads. By irradiating gold nanorods in an aqueous solution comprising cells, the cells can be effectively disrupted due to the increase in temperature of the aqueous solution. FIG. 2 is a schematic illustration comparing the sizes of micro-magnetic beads and exemplary nanomaterials according to embodiments of the invention. The nanomaterials are much smaller than the micro-magnetic beads. Such smaller nanomaterials do not greatly affect the optical properties of the aqueous solution. In addition, even when a small amount of nanomaterials is added to the aqueous solution, the surface area of the nanomaterials that may contact other materials in the aqueous solution significantly increases compared to the same amount of a micromaterial. Thus, the nanomaterial is much more advantageous with respect to transfer of energy efficiently to the solution upon irradiation with a laser.

According to another embodiment, there is provided a method of continuously disrupting cells and amplifying nucleic acids in a single microchamber, the method comprising: introducing a solution containing cells and gold nanorods into a microchamber; irradiating a laser onto the gold nanorods to disrupt the cells; and amplifying a nucleic acid from the disrupted cells in the microchamber.

Figure 3:
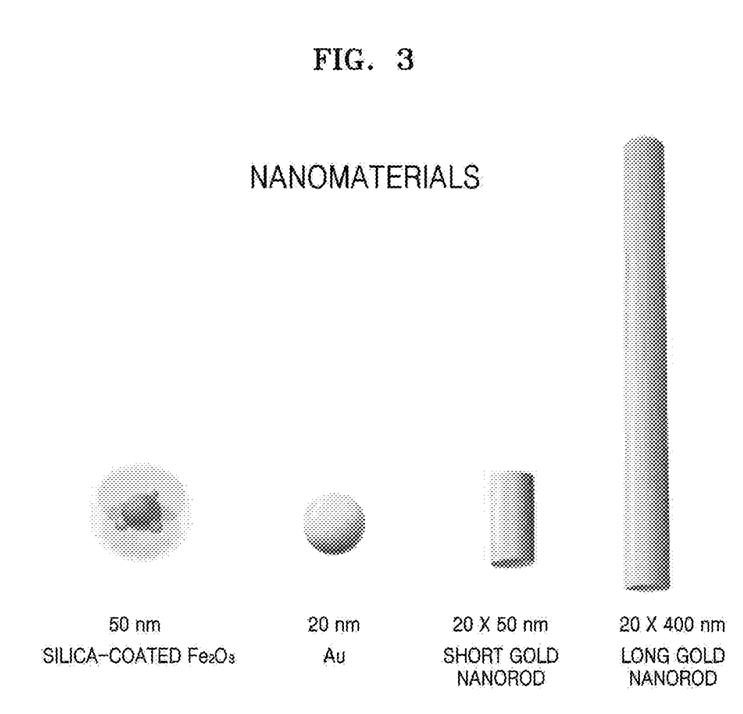
FIG. 3 is a schematic diagram of exemplary nanomaterials.

By replacing magnetic beads with nanomaterials, a system is provided which enables real time PCR detection without the need to remove the nanomaterials. FIG. 3 is a schematic diagram of various exemplary nanomaterials. When a laser is irradiated onto a solution containing gold nanomaterials and cells, the temperature of the solution increases, thereby disrupting the cells and resulting in the release of genetic materials, such as DNA and RNA, into the solution. Gold nanomaterials can be directly applied in real time amplification processes. For the example of using gold nanomaterials in real-time PCR, inclusion of a pre-mixed PCR solution which has been mixed with a sample prior to irradiation with a laser is possible since the gold nanomaterials do not per se optically disturb a PCR apparatus or fluorescent materials. Thus, disruption of cells and amplification of nucleic acids can be continuously performed in a single microchamber. In a conventional procedure, disruption of cells and amplification of nucleic acids are performed in separate microchambers, which increases analysis time and cost, and also increases the possibility of cross-contamination of a sample. The present invention integrates the disruption of cells and the amplification of nucleic acids in order to simplify an analysis procedure and reduce the risk of cross-contamination. For example, real time PCR results can be obtained using a cell disruption and PCR chip into which a sample with a potential pathogen has been initially introduced, without having to transfer the sample to a separate analysis chamber, thereby permitting direct PCR identification of the potential pathogen.

According to yet another embodiment, a solution containing cells and gold nanorods is introduced into a microchamber. The solution containing cells can be any solution comprising a cell, for example, saliva, urine, blood, serum, amniotic fluid, semen, peritoneum fluid, pleura fluid, bone marrow, and a cell culture, but is not limited thereto. After introducing the solution containing the cells and gold nanorods into the microchamber, the mixture can be vibrated to increase the efficiency of cellular disruption.

In one embodiment, a laser is irradiated onto the gold nanorods in order to disrupt the cells. Irradiation of a laser onto the gold nanorods increases the temperature of the solution thereby efficiently disrupting the cells.

The gold nanorods used should be able to absorb light at a specific wavelength. The gold nanorods can have a length of about 10 to about 500 nanometers (nm) and a diameter to length ratio of about 1:2 to about 1:50. The gold nanorods absorb light at a specific wavelength and convert the light energy into heat much more efficiently than spherical gold nanobeads.

The laser can be a pulse laser or a continuous wave laser. If the laser power is too low, efficient disruption of the cells does not occur. The laser power can be about 10 mW or more for a continuous laser and about 1 mJ/pulse or more for a pulse laser. Preferably, the pulse laser has a power of about 3 mJ/pulse or more and the continuous wave laser has a power of about 100 mW or more. When the continuous wave laser has a power less than 10 mW and the pulse laser has a power less than 1 mJ/pulse, sufficient energy to disrupt the cells is not transferred.

The light generated by the laser is preferably in a wavelength range of about 400 nm or more since DNA is denatured or damaged at wavelengths less than about 400 nm. More preferably, the laser light should be generated in a specific wavelength range in which the gold nanorods absorb the laser light. The wavelength range absorbed by the gold nanorods can vary as a function of the diameter to length ratio of the gold nanorods, as demonstrated in the Examples. When short gold nanorods having a diameter to length ratio of about 1:2 to about 1:5 are used, the laser can generate light in a wavelength range of about 700 to about 900 nm. When long gold nanorods having a diameter to length ratio of about 1:10 to about 1:50 are used, the laser can generate light in a wavelength range of about 800 nm or more.

The laser can also generate light that falls within one or more wavelength ranges. That is, the laser light can have one wavelength, or two or more different wavelengths, within the above-described ranges.

The gold nanorods can be prepared using conventional preparation methods known in the art, that include, for example, electrolysis, chemical reduction, optical reduction, and the like. In the electrolysis method, gold nanorods are produced by electrolyzing an aqueous solution containing a cationic surfactant in a static current in order to leach gold clusters from an anode of a gold plate. The cationic surfactant comprises a quaternary ammonium having four hydrophobic substituents bonded to the nitrogen atom such that the compound does not spontaneously form a molecular aggregate, for example, tetradodecylammonium bromide (TDAB). The source of the gold supply is the gold cluster leached from a gold-plated anode. Gold salts such as chloroaurate are not used as the gold source in the electrolysis method. A silver plate is immersed in the solution, and the growth of gold nanorods is facilitated by the generation of ultrasonic waves in the solution during the electrolysis process (Yu, Y.-Y, et al. (1997) *J. Phys. Chem. B,* 101: 6661). In the chemical reduction method, $HAuCl_4$ is reduced with $NaBH_4$ to produce gold nanorods as seed particles which grow in the solution. The length of the gold nanorods produced is dependent upon the ratio of the seed particles to the chloroaurate added to the growth solution and the growth time (Jana, N. R., et al. (2001) *J. Phys. Chem. B,* 105: 4065). In the optical reduction method, chloroaurate is added to a solution similar to the one used in the electrolysis method, and the solution is irradiated with ultraviolet light. A low pressure mercury lamp can be used for the ultraviolet irradiation. Optical reduction produces gold nanorods without producing seed particles. The length of the gold nanorods can be controlled by the irradiation time (Kim, F. et al. (2002) *J. Am. Chem. Soc.,* 124: 14316).

In yet another embodiment, amplification of nucleic acid released from the disrupted cells can be performed without removing the gold nanorods. That is, although the amplification can be performed after removing the gold nanorods, since the gold nanorods do not greatly affect the optical properties of the solution, real-time amplification, for example real time PCR, can be efficiently performed without removing the gold nanorods. Micro-magnetic beads need to be removed in order to perform real time PCR or other amplification methods, whereas gold nanorods do not need to be removed. Thus, the present invention is more suitable for implementation in a Lab-on-a-Chip (LOC) method.

According to one embodiment, amplifying the nucleic acid comprises adding a polymerase chain reaction (PCR) mixture to the microchamber; and performing PCR on the nucleic acid. A PCR mixture can be added directly to the microchamber to perform a PCR. In an embodiment, a general PCR mixture is directly added to a lysate of cells disrupted by the gold nanorods, without any additional steps, and real time PCR is performed on the nucleic acid in the lysate to obtain PCR products. A fluorescent material such as SYBR Green can be added to the PCR mixture to efficiently detect PCR products.

As used herein, "PCR" means a polymerase chain reaction and is a method of amplifying a target nucleic acid from a primer pair specifically binding to the target nucleic acid using a polymerase. PCR is well known in the art and can also be performed using commercially available kit. In addition to PCR, alternative methods of amplifying a nucleic acid include a ligase chain reaction, a nucleic acid sequence-based amplification, a transcription-based amplification system, a strand displacement amplification, a Qβ replicase amplification, and any suitable amplification method known in the art.

A "PCR mixture" means a 1× buffered solution at pH and salt conditions that permit PCR and which further comprises an appropriate concentration of each dNTP, an appropriate concentration of each primer of the primer pair, and an appropriate amount of a suitable DNA polymerase. The PCR mixture may contain any known chemicals used in a buffer for a PCR reaction. An exemplary buffer composition comprises Tris or Tricine at a concentration of about 10 to about 100 mM, buffering at a pH of about 7.0 to about 9.0. A PCR mixture contains $Mg^{2+}$ (e.g., $MgCl_2$ or $MgSO_4$) in the range of about 1 to about 10 mM. The buffer can also contain $K^+$ (e.g., KCl) in the range of 0 to about 50 mM. In some embodiments, the buffer contains components which enhance PCR yield (e.g., $(NH4)_2SO_4$ in the range of 0 to about 20 mM). The PCR mixture can also contain BSA in the range of about 1 to about 100 μg/ml. Primer concentrations can range from about 100 nM to about 1,000 nM for target nucleic acid concentrations ranging from about pM to about nM. Suitable DNA polymerases are well known in the art; many are commercially available individually or as part of a kit. Some examples are Taq DNA polymerase, FastStart Taq DNA polymerase, Pfu DNA polymerases, etc. Leading commercial suppliers of Taq DNA Polymerase include Invitrogen, Applied Biosystems, Promega, Roche, Bioneer and Fermentas. Appropriate concentrations of DNA polymerase are about 0.01 to about 0.1 units/μl. The PCR mixture can also comprise a detection means, for example, SYBR Green I dye. Optimizing a PCR mixture for optimal amplification using a particular combination of conditions, primers, or amplification target is well-known in the art.

According to another embodiment, there is provided an apparatus for disrupting cells and amplifying nucleic acids in a single microchamber, wherein the apparatus comprises: a cell disruption chamber having a sample inlet; a laser attached to the cell disruption chamber; and a heater and a cooler for heating and cooling the cell disruption chamber.

In the apparatus, the cell disruption chamber has a sample inlet through which a sample containing cells or gold nanorods can be introduced. The sample is introduced through the sample inlet. The sample added to the cell disruption chamber is mixed well with the gold nanorods. This mixing can be achieved with a vibrator. A laser is irradiated onto the sample while the mixture of the sample and the gold nanorods is vibrated. The cell disruption chamber is composed of a material through which laser light at the required wavelength can sufficiently pass.

The laser is attached to the chamber.

The heater and the cooler heat and cool, respectively, the cell disruption chamber during an amplification reaction. For example, when a PCR mixture is introduced into the cell disruption chamber, the heater and the cooler control the temperature of the cell disruption chamber according to the conditions of the PCR reaction.

The apparatus may further comprise a reservoir that is connected to the cell disruption chamber via a microchannel that can supply additional solutions to the cell disruption chamber, for example a PCR mixture or an elution buffer. Once the cells are disrupted to release nucleic acids, the reservoir can supply a solution comprising amplification components, for example a PCR mixture to the cell disruption chamber. The supplied amplification components and the released nucleic acids are subsequently used to amplify the nucleic acids.

The apparatus may further comprise a vibrator attached to the cell disruption chamber for the purpose of mixing the sample containing cells and gold nanorods in the chamber. Examples of suitable vibrators include a sonicator, a vibrator using an electric field, a mechanical vibrator, or a piezoelectric material, but are not limited thereto.

According to another embodiment, there is provided a Lab-on-a-Chip (LOC) comprising the apparatus for disrupting cells and amplifying nucleic acids according to the present invention. To implement the apparatus as a lab-on-a-chip apparatus, each functional element can be implemented by a process-on-a-chip element using known microfluidics technology, and known micro-electro-mechanical systems (MEMS) devices. The present invention will now be described in greater detail with reference to the following examples. The following examples are for illustrative purposes only and are not intended to limit the scope of the invention.

EXAMPLES

Example 1

Preparation of Gold Nanorods (1)

In an Erlenmeyer flask, 20 milliliters (mL) of an aqueous solution containing $2.5 \times 10^{-4}$ M $HAuCl_4$ and $2.5 \times 10^{-4}$ M trisodium citrate was prepared. Then, 0.6 mL of a 0.1 M cold $NaBH_4$ solution was added at one time. The color of the solution changed to pink as soon as the $NaBH_4$ solution was added, which indicates the formation of particles. This solution was used as a seed particle solution within 2-5 hours after preparation.

Figure 4:
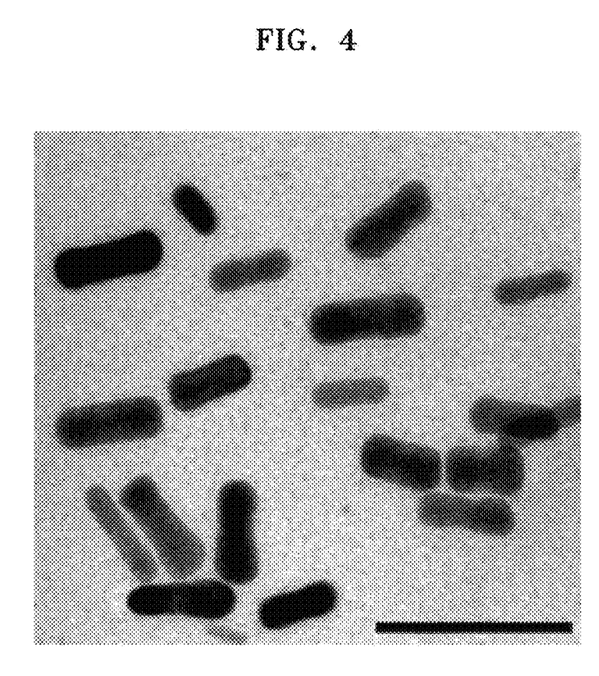
FIG. 4 is a transmission electron microscopic (TEM) image of gold nanorods prepared as described in Example 1, the scale bar represents 100 nm.

In a clear test tube, 10 mL of a growth solution containing $2.5 \times 10^{-4}$ M $HAuCl_4$ and 0.1 M cetyltrimethylammonium bromide (CTAB) was mixed with 0.05 mL of a 0.1 M ascorbic acid solution. Then, 0.025 ml of the seed particle solution prepared above was added to the growth solution without stirring or shaking. The seeded growth solution was left undisturbed for about 40 minutes to obtain gold nanorods. FIG. 4 is a transmission electron microscopic (TEM) image of the resulting gold nanorods. The gold nanorods had a diameter of about 16.4 nm, a length of about 49±7 nm, and a diameter to length ratio of about 1:3. In FIG. 4, the length of the scale bar is 100 nm.

Example 2

Preparation of Gold Nanorods (2)

Figure 5:
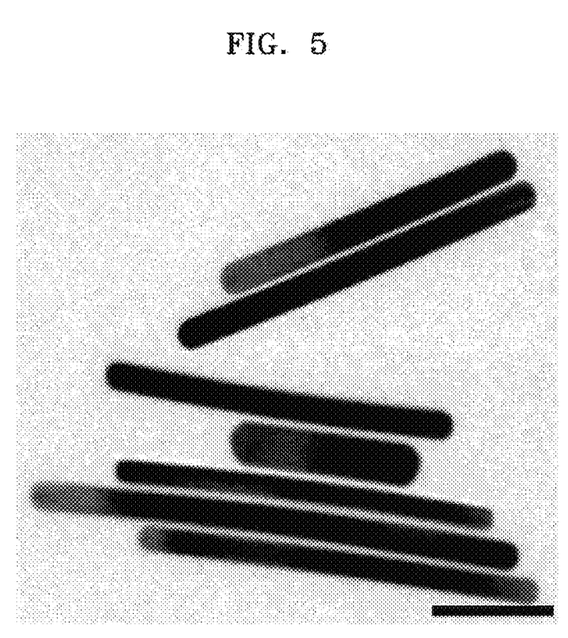
FIG. 5 is a TEM image of gold nanorods prepared as described in Example 2 the scale bar represents 100 nm.

Long gold nanorods were prepared in the same manner as in Example 1, except that the concentration of CTAB in the growth solution was 5 mM and the growth time was 2 hours. FIG. 5 is a TEM image of the resulting gold nanorods, including a scale bar of length 100 nm for reference. The gold nanorods had a diameter of about 15.4 nm, a length of about 254±43 nm, and a diameter to length ratio of about 1:13.7 to about 1:19.3.

Example 3

Measurement of the Absorbance of the Gold Nanorods

Figure 6:
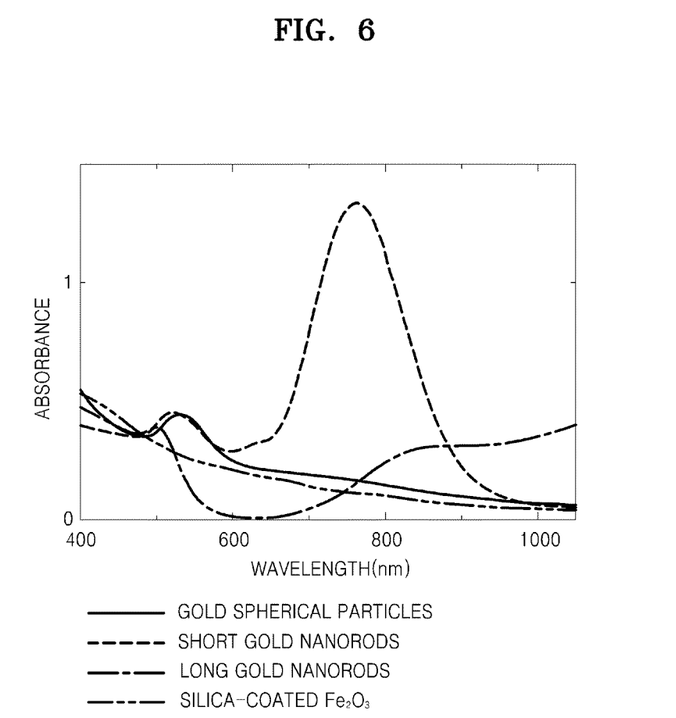
FIG. 6 is a graph comparing the absorbance of the gold nanorods of FIGS. 4 and 5 with other nanomaterials, and measured using a laser in a wavelength range of about 300 to about 1400 nm.

The absorbance of the gold nanorods prepared in Examples 1 and 2 was measured using a laser in a wavelength range of about 300 to about 1400 nm and the results were compared to the results obtained with other nanomaterials. For the measurement, a 1 mg/mL rod solution was added to a 1 $cm^3$ quartz cell, which was then placed in an ultraviolet-visible (UV-Vis) spectrometer. The results are illustrated in FIG. 6. Referring to FIG. 6, the gold nanorods prepared in Example 1, with a diameter to length ratio of about 1:3, demonstrate a high level of absorbance in the wavelength range of about 750 to about 910 nm. In contrast, the gold nanorods prepared in Example 2, with a diameter to length ratio of about 1:13.7 to about 1:19.3, demonstrated a high level of absorbance at a wavelength of about 910 nm or more. Both the short and the long gold nanorods had a higher absorbance at a wavelength of about 808 nm than the other nanomaterials. These results indicate that cells can be efficiently disrupted in the presence of gold nanorods by adequately controlling the laser wavelength range according to the diameter to length ratio of the gold nanorods.

Example 4

Increase in the Temperature of an Aqueous Solution by Gold Nanorods

The gold nanorods prepared in Example 2 were used to determine whether they could increase the temperature of an aqueous solution. 8 mg of the gold nanorods prepared in Example 2, was added to 1 mL of distilled water, and a laser was irradiated on the solution at a wavelength of about 808 nm for about 0 to about 120 seconds. The temperature of the aqueous solution was subsequently determined. The laser power was 1.5 W. Distilled water (DW) and distilled water with micro-magnetic beads (Dynabeads® M-270 Carboxylic Acid, DYNAL, Norway) at a concentration of 8 mg/mL were used as control groups. The results are illustrated in FIG. 7.

Figure 7:
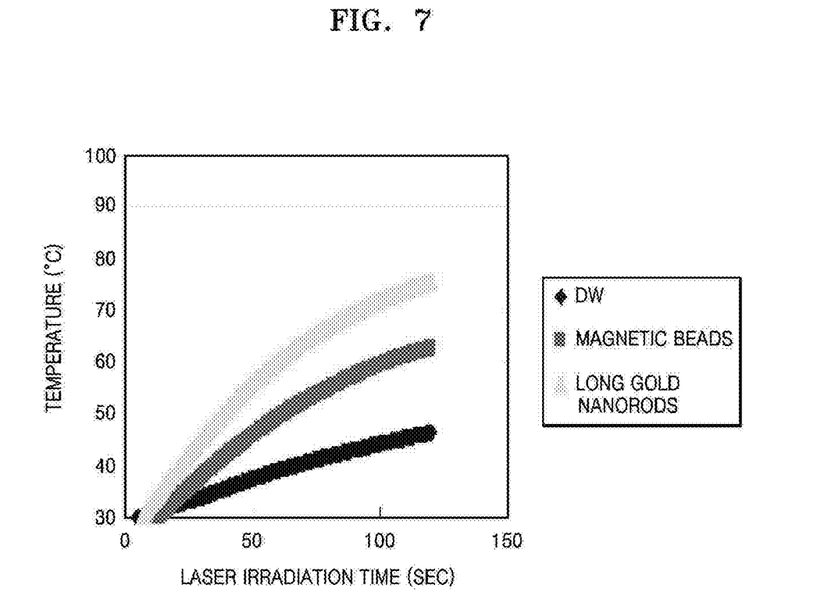
FIG. 7 is a graph of laser irradiation time versus temperature for distilled water, an aqueous solution containing micro magnetic beads, and an aqueous solution containing gold nanorods, measured using a laser at a wavelength of 808 nm.

Referring to FIG. 7, the gold nanorods and the micro-magnetic beads had a significant effect on heating the aqueous solution as compared to DW alone. More specifically, the heating effect of the gold nanorods was shown to be better than that of the micro-magnetic beads.

Thus, it is expected that cells can be more efficiently disrupted using gold nanorods.

Example 5

Effect of Gold Nanorods on PCR Reactions

The PCR inhibition effects of gold nanorods were investigated. The 20 nm gold spherical particles illustrated in FIG. 3, and the gold nanorods prepared in Example 2, were used as gold nanomaterials. Distilled water (DW), and distilled water containing various particles, for example micro-magnetic beads (Dynabeads® M-270 Carboxylic Acid, DYNAL, Norway) at 8 mg/mL were used as control groups. PCR was performed using a TMC1000 (Samsung), which is an apparatus for conducting quantitative PCR on a silicon-based chip. The template DNA used in the experiment was genomic DNA purified from E. coli BL21. The PCR primers used were a forward primer (YCCAKACTCCTACGGGAGGC; SEQ ID NO: 1), and a reverse primer (GTATTACCGCRRCT-GCTGGCAC; SEQ ID NO: 2). LIGHTCYCLER® FastStart DNA Master SYBR Green I (Roche) was added to the PCR mixture in order to observe real time PCR. The PCR mixture was, briefly, composed of 1×PCR buffer (75 mM Tris HCl pH 9.0, 15 mM $(NH_4)_2SO_4$), 2.5~5.0 mM $MgCl_2$, 200 µM of each dNTP, 0.2 µM of each primer, 0.1 mg/ml BSA, 0.01~0.1 u/µl FASTSTART Taq DNA polymerase, and 0.5× SYBR Green I dye. PCR was performed for one cycle at 94° C., 1 min; and followed by 40 cycles at 94° C., 5 sec; 62° C., 5 sec; and 72° C., 20 sec. The resulting PCR products were monitored in real time using the TMC1000 (Samsung).

Figure 8:
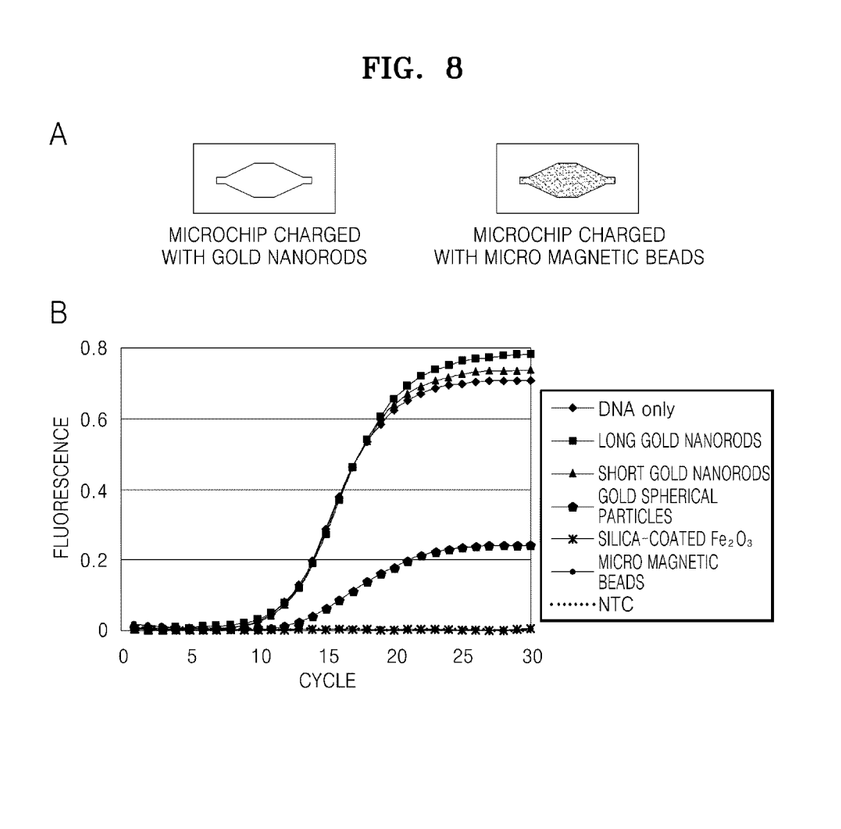
FIG. 8 is a graph illustrating the effects of various particulate materials, including micro-magnetic beads and gold nanorods, on real time PCR efficiency when using purified genomic DNA from *E. coli*.

Referring to FIG. 8A, the micro-magnetic beads look opaque in a PCR chip, while the gold nanorods of the present invention are clear, indicating that the gold nanorods are optically non-problematic.

FIG. 8B is a graph illustrating the results of the real time PCR for each sample: no beads (diamond), short gold nanorods prepared in Example 1 (triangle), long gold nanorods prepared in Example 2 (square), micro-magnetic beads (circle), 20 nm gold spherical particles (square), and silica coated $Fe_2O_3$ (X). Each type of particle was present at a concentration of about 8 mg/mL. Referring to FIG. 8B, no fluorescence was detected in the sample containing the micro-magnetic beads, and the highest fluorescence was observed in the sample containing the gold nanorods. The level of fluorescence of the SYBR Green dye was decreased in samples containing the 20 nm gold spherical particles (square). Silica coated $Fe_2O_3$ (X) completely inhibited the PCR reaction, as evidenced by a total lack of signal.

Thus, it can be seen that since gold nanorods do not inhibit real time PCR monitored using the SYBR Green dye, real time PCR can be performed directly without removing the gold nanorods.

Example 6

DNA Extraction and Subsequent Real Time PCR in a Single Chamber

Figure 9:
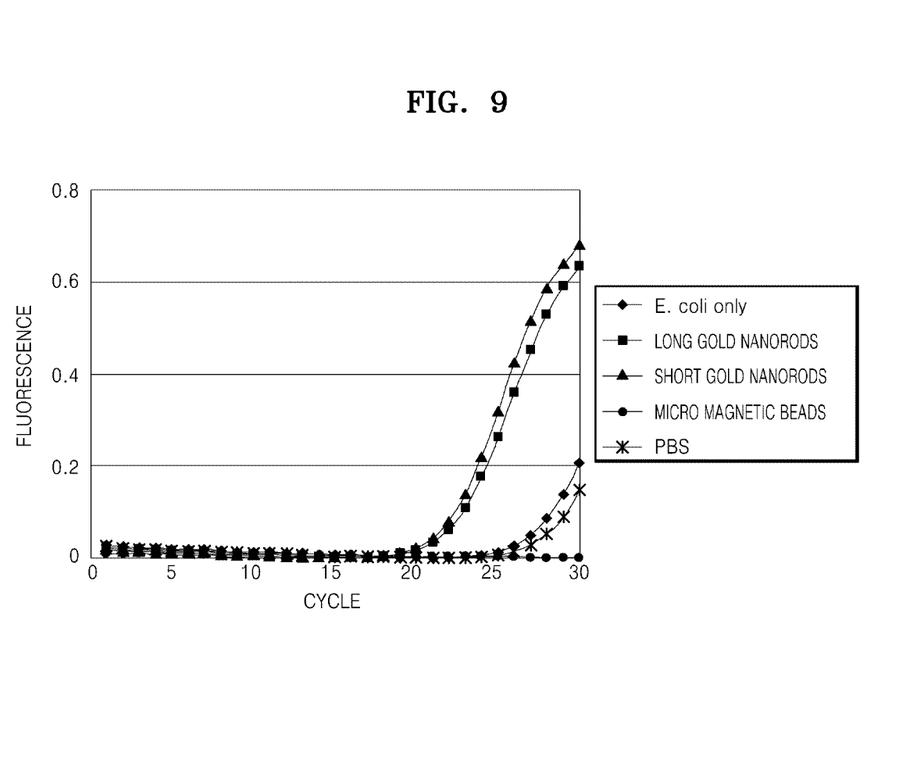
FIG. 9 is a graph illustrating the effects of micro-magnetic beads and gold nanorods on the efficiency of genomic DNA extraction from *E. coli* and subsequent real time PCR when both processes are performed in a single microchamber.

It was investigated whether lysis of *E. coli* to extract genomic DNA followed by subsequent real time PCR could be continuously performed in a single chamber. *E. coli* BL21 and the PCR conditions described in Example 5, were used to perform real time PCR in a single chamber immediately following lysis of *E. coli* to extract genomic DNA from the *E. coli*. FIG. 9 is a graph illustrating the results of real time PCR using genomic DNA extracted according to the type of added particles: no beads (diamond), long gold nanorods prepared in Example 2 (square), short gold nanorods prepared in Example 1 (triangle), and micro magnetic beads (circle). Threshold cycle (Ct) and Rn values for the real time PCR results are listed in Table 1. Ct reflects the cycle number at which the fluorescence generated for an individual reaction crosses a fixed threshold during real time amplification of DNA. The Ct value can be used to calculate the initial amount of DNA present in a sample. For example, the higher the initial amount of DNA in the sample, the sooner the accumulated product is detected in the PCR process (based on fluorescence), and the lower the Ct value. Further, under the same experimental conditions and identical initial amounts of DNA, a smaller Ct value can reflect a higher PCR efficiency. A cycle difference between samples of 3.5 indicates a DNA concentration difference of about 100-fold. The Rn value is the relative fluorescence intensity generated from the DNA product amplified by PCR.

TABLE 1

| Sample | Ct | Rn |
|---|---|---|
| *E. coli* only | 26.84 | 0.208 |
| *E. coli* + long gold nanorod | 22.07 | 0.634 |
| *E. coli* + short gold nanorod | 21.60 | 0.679 |
| *E. coli* + micro magnetic bead | N/A | 0.001 |
| PBS | N/A | 0.148 |

Referring to FIG. 9 and Table 1, when micro-magnetic beads are used, no PCR products are observed, indicating that the micro-magnetic beads failed to lyse the *E. coli* efficiently and/or inhibited the PCR reaction. In contrast, based on the Ct values, the long or short gold nanorods of the present invention yielded about 100 times more DNA from *E. coli* as compared to samples containing *E. coli* without beads. Further, the results were obtained by real time PCR without any inhibition of the PCR reaction.

Thus, the method of continuously disrupting cells and amplifying nucleic acids in a single microchamber as described herein, can be used to increase the efficiency of amplifying nucleic acid from disrupted cells. Since efficient PCR is possible without removing the gold nanorods after disrupting the cells, the method of the present invention can efficiently disrupt cells and amplify nucleic acids in the same chamber.

Advantages of the invention include removal of gold nanorods is not required, various fluorescent materials including SYBR Green can be used together, preparation costs are low, and the gold nanorods can be used in smaller amounts as compared to micro-magnetic beads and still provide the same effects. In addition, gold nanorods are not harmful to humans and they are eco-friendly, thereby making them safe materials for use.

In addition, it is not necessary to remove the nanorods for the purpose of purifying and concentrating the DNA products after PCR. Thus, it is expected that the present invention can also be applied to post-PCR processes such as, analysis using other enzymes, nucleotide sequence analysis using amplified DNAs, and the like.

Moreover, the present invention can be implemented in a LOC that can be used to easily diagnose pathogens causing infectious diseases or, diagnose genetic diseases and the like, by rapidly analyzing genetic materials.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for disrupting cells and amplifying nucleic acids in a single chamber comprising:
   a cell disruption chamber comprising a sample inlet, and gold nanorods contained within the cell disruption chamber;
   a laser attached to the cell disruption chamber, wherein the laser is for generating light at a wavelength absorbed by the gold nanorods; and
   a heater and a cooler for heating and cooling the cell disruption chamber during a nucleic acid amplification reaction.

2. The apparatus of claim 1, further comprising:
   a reservoir which is connected to the cell disruption chamber via a microchannel.

3. The apparatus of claim 1, further comprising
   a vibrator attached to the cell disruption chamber,
   wherein the vibrator is for mixing a sample in the cell disruption chamber.

4. The apparatus of claim 3, wherein the vibrator is a sonicator, a vibrator using an electric field, a mechanical vibrator, or a piezoelectric material.

5. The apparatus of claim 1, wherein the gold nanorods have a diameter to length ratio ranging from about 1:2 to about 1:50.

6. The apparatus of claim 1, wherein the gold nanorods have a length ranging from about 10 to about 500 nm.

7. The apparatus of claim 1, wherein the gold nanorods have a diameter to length ratio ranging from about 1:2 too about 1:5 and the laser is for generating light at a wavelength in the range of about 700 nm to about 900 nm.

8. The apparatus of claim 1, wherein the gold nanorods have a diameter to length ratio ranging from about 1:10 to about 1:50 and the laser is for generating light at a wavelength in the range of about 800 nm or more.

9. The apparatus of claim 1, wherein the cell disruption chamber is composed of a material through which the generated laser light can sufficiently pass.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
yccakactcc tacgggaggc                    20

<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
gtattaccgc rrctgctggc ac                 22